United States Patent [19]
Sivers

[11] Patent Number: 6,072,851
[45] Date of Patent: Jun. 6, 2000

[54] HELICAL COMPUTERIZED TOMOGRAPHY SYSTEM AND METHOD PROVIDING QUALITY IMAGES WITH FASTER SCANS

[75] Inventor: E. Anne Sivers, Lake Oswego, Oreg.

[73] Assignee: Kabushiki Kaisha Toshiba, Kawasaki, Japan

[21] Appl. No.: 08/476,984

[22] Filed: Jun. 7, 1995

Related U.S. Application Data

[63] Continuation of application No. 08/405,396, Mar. 15, 1995, abandoned, which is a continuation of application No. 07/991,050, Dec. 15, 1992, abandoned.

[51] Int. Cl.[7] ........................................................ A61B 6/03
[52] U.S. Cl. ............................................. 378/15; 378/901
[58] Field of Search ............................... 378/14, 15, 901; 364/413.15, 413.18, 413.21

[56] References Cited

U.S. PATENT DOCUMENTS

| | | | |
|---|---|---|---|
| 4,965,726 | 10/1990 | Heuscher et al. | 364/413.19 |
| 5,262,946 | 11/1993 | Heuscher | 364/413.18 |
| 5,291,402 | 3/1994 | Pfoh | 364/413.14 |

*Primary Examiner*—David V. Bruce
*Attorney, Agent, or Firm*—Finnegan, Henderson, Farabow, Garrett & Dunner, L.L.P.

[57] ABSTRACT

A computerized tomography system is provided with a gantry that is rotatable in an X-Y plane transverse to a Z reference axis. The gantry has an opening through which a support on a couch is linearly movable along the Z-axis. An X-ray source directs rays across the gantry opening to a pair of arrays of X-ray detectors. Doing a rapid scan the gantry is rotated as the support is moved linearly so that a helical path is followed by the X-ray source. The resultant dual array data is combined and processed to generate successive quality X-Y planar images.

10 Claims, 15 Drawing Sheets

HELICAL COMPUTERIZED TOMOGRAPHY SYSTEM AND METHOD PROVIDING QUALITY IMAGES WITH FASTER SCANS

This application is a continuation of application Ser. No. 08/405,396 filed Mar. 15, 1995, now abandoned, which is a continuation of application Ser. No. 07/991,050 filed Dec. 15, 1992, now abandoned.

BACKGROUND OF THE INVENTION

The present invention relates to tomography systems and operating methods and more particularly to systems and methods for implementing helical computerized tomography.

Computerized tomography (CT) is a well established technology for imaging cross-sectional planes of objects nondestructively.

CT systems generally may direct source electromagnetic radiation through an object and detect the radiation altered by the object to provide information about the nature of the object. Normally, a CT system comprises a source of X-radiation, an array of X-ray detectors, a mechanism for rotating the source and detectors continuously around a reference axis extending through the object, a couch for advancing the object continuously along the reference axis, data collection hardware for converting detector signals to digital records, data processing hardware for reconstructing a plurality of two-dimensional images from the digital records, and imaging hardware for displaying and recording the images.

In CT systems designed to generate planar scans, X-ray slice data is collected by a planar array of detectors placed opposite an X-ray source, both of which rotate rigidly in a plane around a stationary object. Alternatively, the X-ray source and the detectors may remain stationary while the object rotates about its own axis.

Standard planar scan CT systems collect a plurality of two-dimensional cross-sectional planes (slices) by rotating the radiation source and one linear array, composed of discrete detector elements, through either 180° or 360° (depending upon the geometry of the source/detector hardware). The rotation is then stopped and the object is advanced parallel to the axis of rotation, where the operation is repeated. The thickness of such a CT slice is determined by the thicknesses of the radiation source and the detectors. To obtain continuous slices, the object is advanced at most by a distance equal to the beam thickness.

The data obtained for each slice by a 360° rotation is processed by a mathematical reconstruction algorithm to produce a two-dimensional image of the slice. A 360° rotation provides more data than the minimum required data set (180° rotation plus the angle of the X-ray fan), but the redundant data is useful since it minimizes inconsistencies between readings taken at the beginning and at the end of the scan. The incremental planar scan procedure produces good images but it is time-consuming.

Data has been collected faster and more efficiently by continuously advancing the object along its axis while the source and detectors also rotate continuously. CT systems for which the object is incremented continuously are typically called "helical" CT systems because the motion of the radiation source as a function of time follows a helical path with respect to a coordinate system fixed in the object being imaged. Data collection speed is maximized if the object is advanced continuously, but the total increment must be much less than the nominal beam thickness if relatively artifact-free images are to be obtained.

The resulting helical data set is less than ideal because data fans taken 360° apart do not lie in the same plane, but if the translational distance is comparable to the slice width of the X-ray beam, satisfactory images can be constructed. Even though single-detector-array, helical scans are faster than planar scans, they are still too slow for many purposes. Thus, as one particularly important example, the fastest known helical CT systems, designed for use in medical tomography, have been too slow to provide data collection for a significant volume of the human chest during a single breath hold, i.e. about 40 seconds.

SUMMARY OF THE INVENTION

The present invention is directed to a helical computer tomography system that is structured to provide high quality images significantly faster than known systems.

A helical computerized tomography system comprises a couch having a support for a patient extending along a reference Z-axis for radiation scanning. A gantry has an opening through which relative linear movement of the patient and gantry occurs for radiation scanning. Means are provided for rotating one of the gantry or the couch support about the Z-axis, and means are provided for moving the other of the gantry and the couch support linearly in the Z direction.

The gantry has a radiation source and an arrangement of detectors disposed in diametrically opposite locations so that a generally fan shaped pattern of scanning rays extend from the source to the detector arrangement in a solid X-Y reference plane that is transverse to the Z-axis. The radiation detector arrangement has a first array of detectors disposed along a first X-Y reference plane at a first Z position, and at least a second array of detectors disposed along a second X-Y reference plane at a second Z position so that the first and second arrays are substantially juxtaposed.

A computer based operating system includes a digital computer, means for controlling power supplied to the radiation source, and means for controlling the couch and the gantry to control the relative linear speed of the patient along the Z-axis with respect to the plane of the radiation source and to control the relative rotational speed of the radiation source with respect to the patient. Further, means are provided for processing signals from the detectors for coupling to the digital computer.

The computer has means for storing the detector signals as representations of data for each detector in each array over time during a system scan, and means for combining stored detector data for the first and second detectors correlated to each of successive X-Y slices to produce a first set of image data for each of the successive slices. Means are provided for convolving and backprojecting the first set of image data to produce an accurate image data set for storage and/or output to an image display system.

BRIEF DESCRIPTION OF THE DRAWINGS

The accompanying drawings, which are incorporated in and constitute a part of this specification, illustrate a preferred embodiment of the invention and together with the description provide an explanation of the objects, advantages and principles of the invention. In the drawings.

DESCRIPTION OF THE INVENTION

Figure 1:
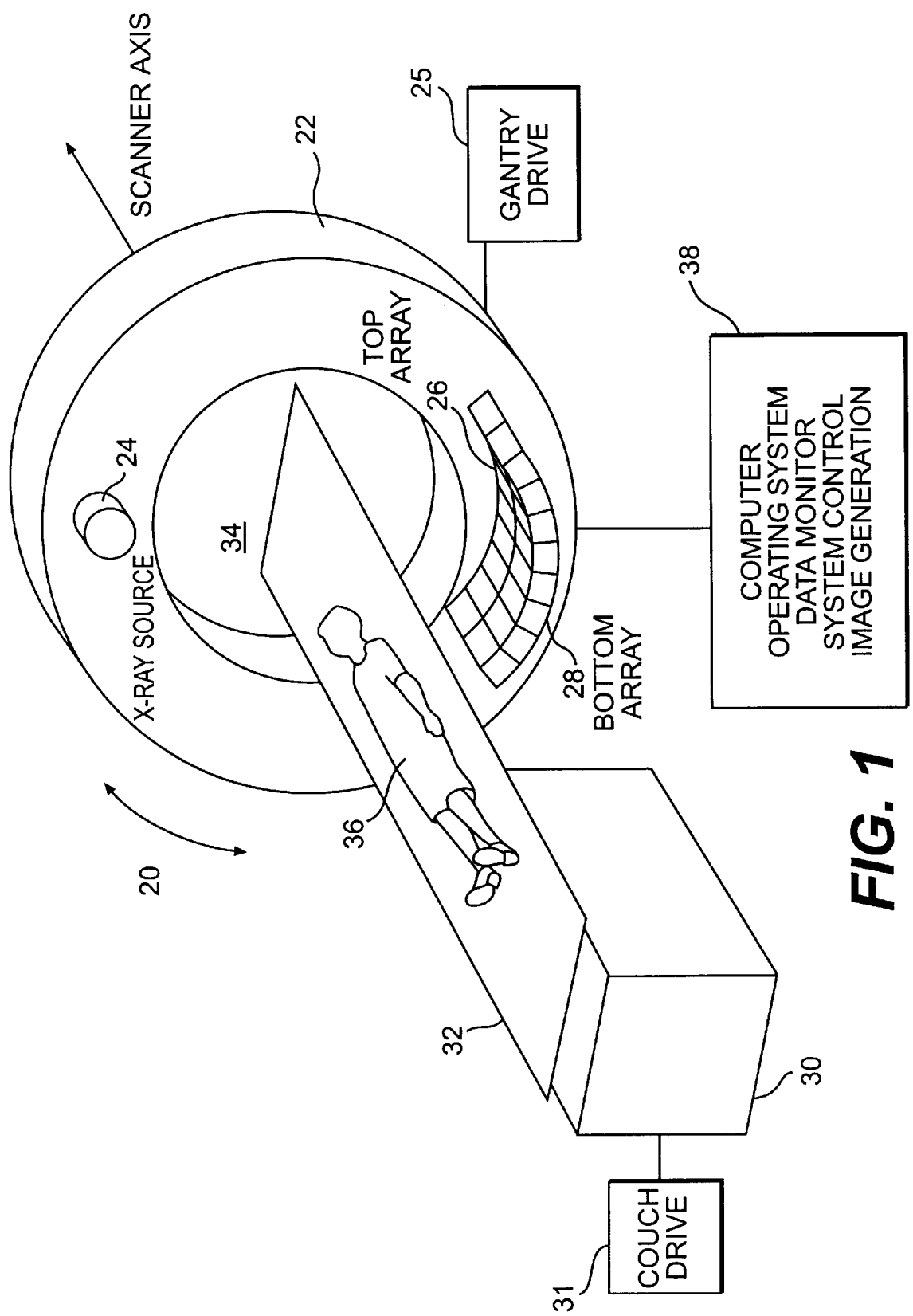
FIG. 1 is a schematic perspective view of a helical, CT system structured in accordance with the principles of the invention.

A tomography system 20 shown in FIG. 1 and arranged in accordance with the invention includes a gantry 22 that is suitably supported for clockwise or counterclockwise rotation. An X-ray source 24 and top and bottom detector arrays 26 and 28 are disposed on the gantry 22 in diametrically opposite positions.

Each detector array 26 or 28 is provided with a plurality of conventional detector elements disposed on an inwardly facing circumferential surface of the gantry 22. The detector elements in each array 26 or 28 are preferably arranged in a single row that extends over an arcuate portion of the inwardly facing gantry surface.

Accordingly, each detector element of each array 26 or 28 faces the X-ray source 24 along a reference line (ray) that forms an angle α with the ray for the centrally located detector element in that array 26 or 28. The absolute magnitude of the angle α increases with increasing distance of the detector elements in either arcuate direction away from the centrally located detector element.

Functionally, each detector element first converts incident radiation to a light signal. In turn, the light signal is converted to an electrical signal for subsequent electronic processing.

A couch 30 is provided with a top member or table 32 that is horizontally driven by a conventional drive 31 through an opening 34 in the gantry 22. A patient 36 lying on the couch table 34 car thus be advanced through the gantry opening 34 for scanning by X-rays generated by the source 24 and received by the dual detector arrays 26 and 28.

In this embodiment, the gantry 22 is rotatable about the patient 36 to enable 360° scans. In industrial application of the invention, a structure (not shown) equivalent to the couch 30 may be rotated within a gantry that is movable in parallel to the Z-axis.

For reference purposes, a longitudinal axis along and through the center of the patient is designated as the Z-axis. A reference plane extending transversely to the Z-axis and through the X-ray source 24 and the detector array structure is designated as the X-Y reference plane.

The X-axis extends horizontally and transversely to the Z-axis. The Y-axis extends vertically and transversely to the Z-axis.

The X-ray source 24 generates respective fan-shaped patterns of rays that are respectively directed toward the dual detector arrays 26 and 28 within a solid X-Y reference plane. For reference purposes, the ray disposed along the midline of the fan pattern forms an angle θ with the X-axis and accordingly is a function of the gantry rotation.

TOMOGRAPHY OPERATING SYSTEM

An operating system 38 is provided for the tomography system 20 to perform data monitoring functions, to perform system control functions, and to generate images for storage or display or other output.

Figure 2:
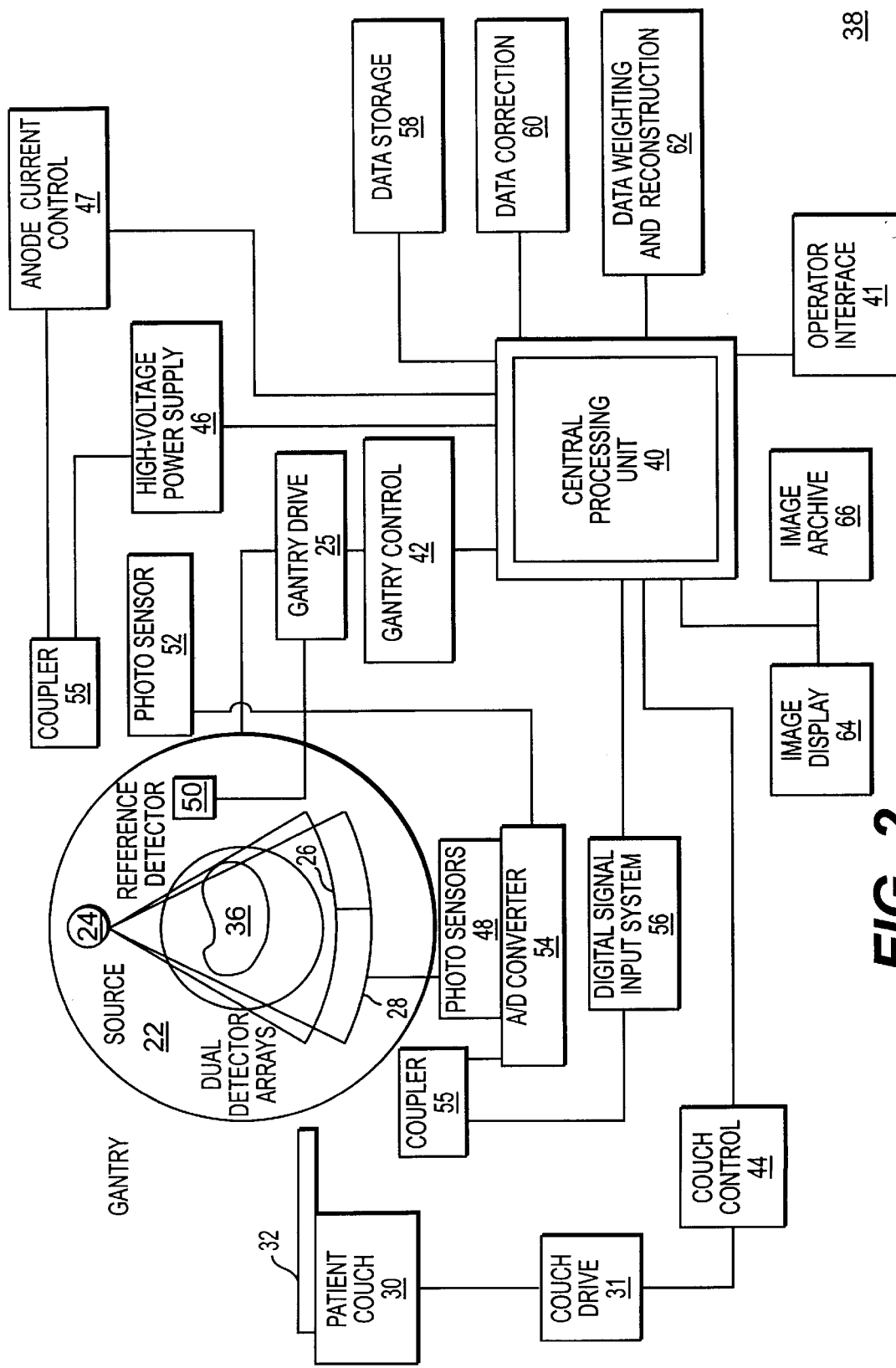
FIG. 2 is a more detailed block diagram of a digital computer based system employed in FIG. 1 to operate the CT system, i.e., to monitor data, control the CT system and generate images.

As shown in greater detail in FIG. 2, the operating system 38 includes a digital computer having a central processing unit (CPU) 40. Since the tomography system 20 performs X-ray scanning over a helical path, it is characterized as a helical computerize tomography system. The X-ray source 24 is mounted on the gantry 22 and is rotated therewith by a conventional drive 25 (FIG. 1) either clockwise or counterclockwise around the Z-axis. The dual detector arrays 26 and 28, denoted TOP and BOTTOM, are rigidly attached to the gantry 22 and rotate with the source 24, with respective fan-shaped, planar X-ray beams extending therebetween in a solid reference scanner plane. The patient couch 30 is controlled by the CPU 40 through a couch control 44 to move the patient 36 preferably at a constant velocity parallel to the Z-axis, either into or out of the scanner plane.

At any instant of time, the fan-shaped X-ray beams intersect respective planes within the patient 36. The plane that is further from the patient couch 30 is denoted the TOP plane corresponding to TOP array 26. The plane that is closer to the patient couch 30 is denoted the BOTTOM plane corresponding to the BOTTOM array 28.

As a function of time, the X-ray source 24 describes a helix about the Z-axis centered and fixed in the patient. As the gantry 22 rotates at a preferably constant angular velocity about its axis (Z-axis) and the couch table 32 translates at a preferably constant velocity parallel to the Z-axis, the light produced by the interaction of X-rays within each detector element is converted to an electrical current by photo-sensors 48.

At periodic intervals, the current from each detector is sampled and the resulting signals are converted to digital data signals by analog-to-digital (A/D) converters 54 preferably disposed at the gantry location. The digital signals are transmitted from the gantry 22 by an electromagnetic or optical coupler 55 to a digital signal input system 56 for the CPU 40 and stored by the CPU 40 in a storage unit 58 as a function of collection time, detector number, and detector array. The stored data is corrected by data correction procedures 60 for physical and timing irregularities, and is subsequently sorted, and reconstructed to produce tomographic images.

The CPU 40 controls the scanner, i.e. the gantry 22, through a control unit 42 in response to commands entered by the user through an operator interface 41. The CPU 40 sets and monitors the X-ray source voltage from a high-voltage power supply 46 and sets and monitors the anode current for the X-ray source 24 through an anode current control 47.

Since the gantry 22 is driven to rotate continuously once activated, a conventional slip ring or similar device is used to transmit power to the X-ray source 24.

In addition to the data signal from the dual-array detectors 26 and 28, the CPU 40 also receives signals from reference detector 50, which monitor X-ray flux variations as a function of time. Light signals from the reference detector 50 are converted to electrical analog signals by photo-sensor 52, and, in turn, the analog signals are converted to digital signals by the A/D converters 54. The digital signals derived from the reference detector 50 are also transmitted from the gantry 22 through the optical or electromagnetic coupler 55. The digital data for the reference detector 50 is stored by the CPU 40 in the storage unit 58 for further processing. In controlling the velocity of translation of the patient couch table 32 through the couch control 44 and the velocity of rotation of the gantry 22 through the gantry control 42, the CPU 40 synchronizes the rates of rotation by a feedback control system that senses the angular velocity of the gantry 22 and the linear couch table velocity and preferably adjusts the velocity of the couch table 32 as a function of the gantry velocity. The absolute velocities of both the gantry 22 and the couch table 32 are recorded as functions of time in the storage unit 58 and used to normalize the actual intervals of data collection.

In operation, data is collected for the duration of the breath hold by the patient 36. The collected data is stored by the CPU 40 as a function of collection time, detector element, and detector array. Data correction is provided by the data correction software 60 (and/or hardware, if desired) for physical irregularities such as, but not limited to, time variations in X-ray flux, time variations in gantry and couch velocity, spatial variations in X-ray flux, X-ray energy spectrum, X-ray source shape, detector element shape, and electronic channel cross-talk.

The natural logarithm of the corrected data is computed, and the data is reconstructed by weighting and reconstruction software 62 (and/or hardware, if desired) to produce CT images of the patient 36. Reconstructed images are displayed and manipulated on an image display 64 and stored in an image archive 66.

DATA PROCESSING PROCEDURE FOR IMAGE RECONSTRUCTION

The data generated by the X-ray detector arrays 26 and 28 corresponds to a helical path followed by the scanning X-ray source 24 relative to the patient 36 as the gantry 22 rotates and the couch table 32 advances linearly. To construct X-Y plane images from the helical path data after storage in the memory 58 as previously described, it is preferred that each of a series of images for a patient scan be reconstructed from a slice (i.e. a solid X-Y reference plane of predetermined thickness) of stored data.

In a first embodiment of the invention, the data slice preferably has a thickness corresponding to the distance the patient 36 advances along the Z-axis during a complete revolution of the X-ray source 24. In a typical application, the slice thickness for a complete revolution scan may be about 1 millimeter.

Figure 3:
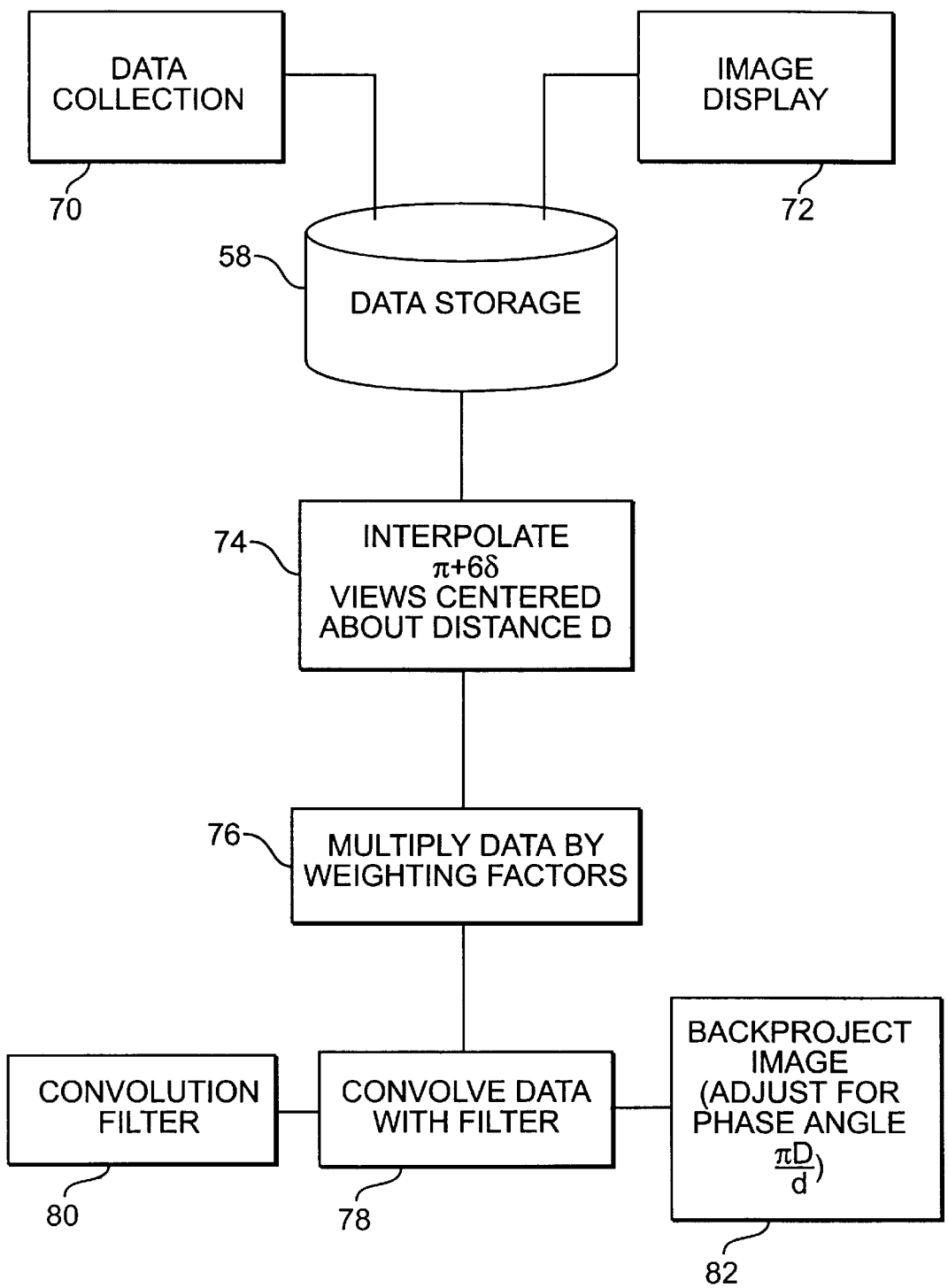
FIG. 3 shows a flow diagram for image reconstruction performed by the system of FIG. 2 in accordance with the invention.

In FIG. 3, there are shown basic components of the procedures 62 for weighting data and reconstructing images in accordance with the invention. A block 70 generally designates the collection of X-ray detector data previously described. A display 72 is provided for processing reconstructed image data for display as sequential two-dimensional images along the direction of patient movement, as a combined three-dimensional image for an entire helical scan, or in any other form available from the image processing software employed by the user.

The data storage unit 58 is also shown to illustrate its relationship to the procedures 62. For a single reconstructed slice, data is addressed in a two dimensional array indexed by view angle $\theta$ (i.e. position of the X-ray source 24) and detector angle $\alpha$ (i.e. angle between detector ray and the Z-axis). Since the generated data contains "redundancies", i.e. two detector signals from respective corresponding detectors in the two arrays 26 and 28 correspond to the same detector angle $\alpha$ but different Z positions within the slice, the collected data is first interpolated to obtain a single set of image data for further processing. Thus, an interpolation component 74 of the procedures 62 selects detector data for interpolation and weighting.

The data is processed for a set of paired views taken by the respective detectors 26 and 28 at the same angle and located on opposite sides of the midplane in the X-Y slice being processed. The data is interpolated for each pair of views to the midplane by the block 74, and it is then weighted by a weighting component 76 thereby providing raw reconstructed image data for further processing. In the first embodiment, each data item is preferable weighted inversely proportional to the distance of the data item from the midplane of the slice.

A second embodiment described subsequently herein provides half scan reconstruction (i.e., a reconstruction using the minimal data rotation set of 180 degrees plus the X-ray fan angle) and employs interpolation and weighting like that just described.

Raw image data generated by the block 76 is convolved by a block 78 in accordance with a conventional convolution filter 80. Convolving modifies the raw data to enable back-projecting an accurate image.

A backprojector component 82 processes the convolved image data to generate an output image, i.e. a two-dimensional array of grayscale values for the reconstructed image. Each pixel in the array may, for example, have a grayscale value between 0 and 256. Successive images for successive slices are stored in the unit 58 for display by the image display 72 as previously described.

IMAGE RECONSTRUCTION PROCEDURES— GREATER DETAIL

Figure 4:
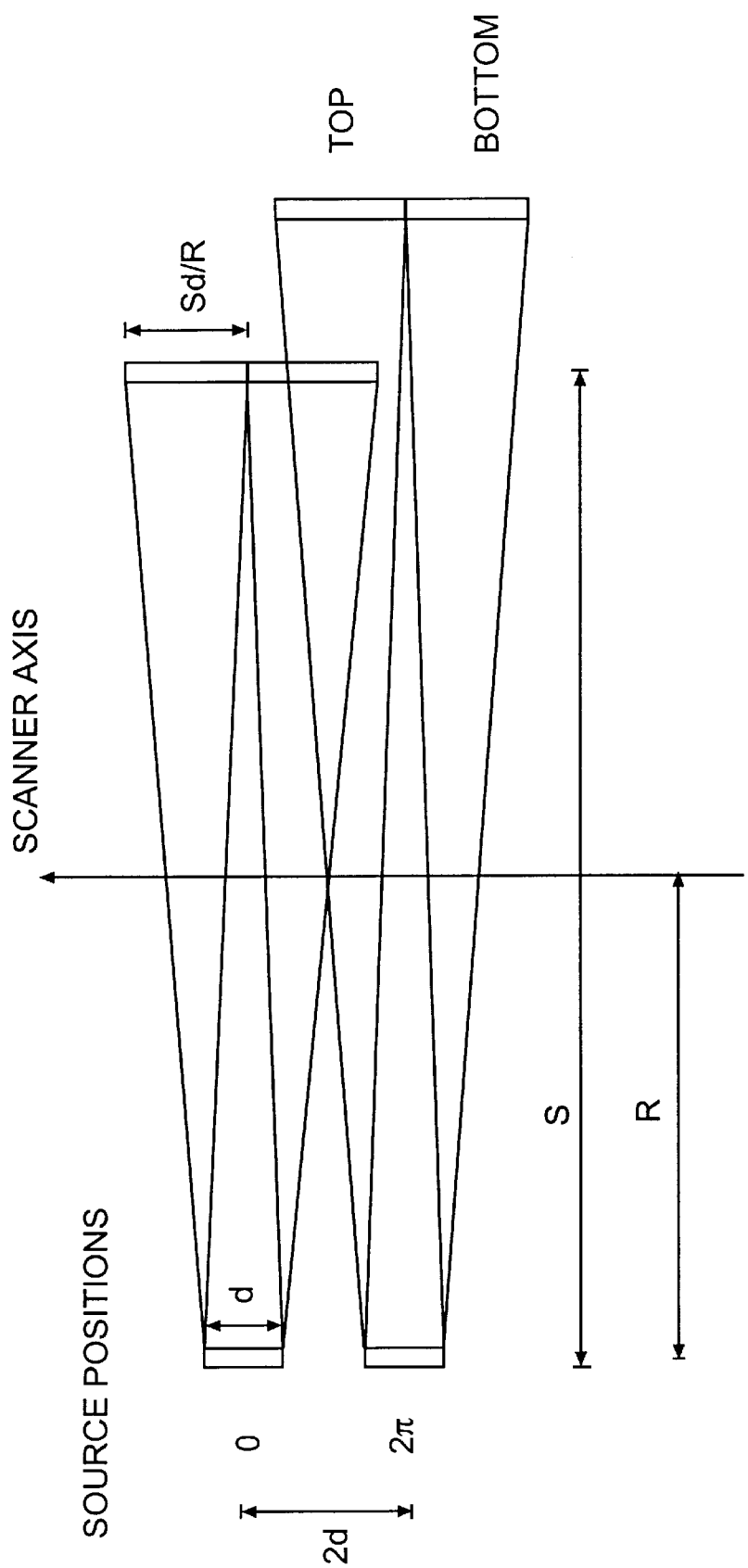
FIG. 4 is an illustration of dual-detector arrays, each of width Sd/R, offset by Sd/(2R) from an X-ray midplane, with a detector location offset in the 360° position for purposes of illustration.
Figure 5:
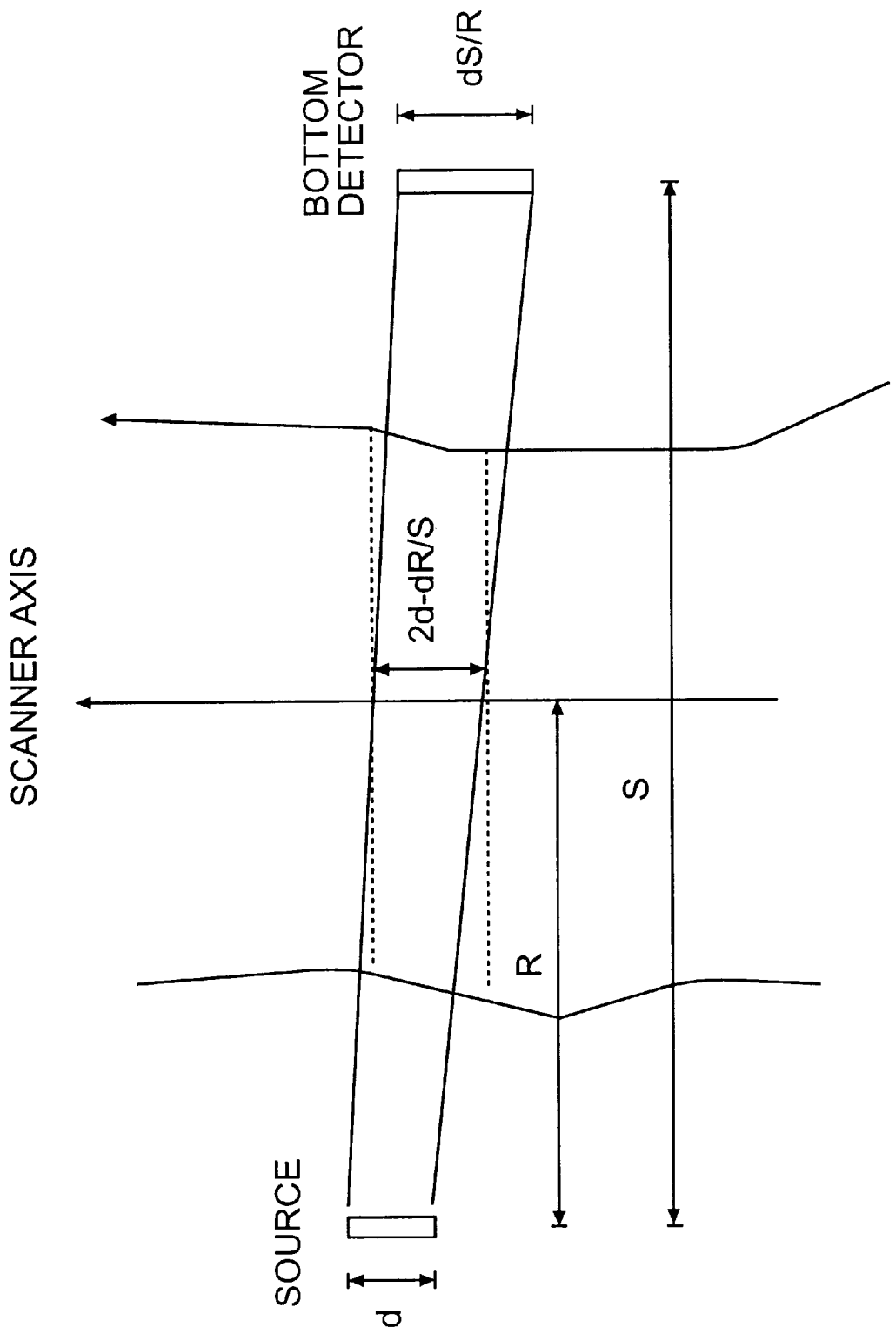
FIG. 5 is an illustration of the beam profile from the BOTTOM detector array of width Sd/R, offset from X-ray midplane by Sd/(2R) with an effective beam width of 2d-Rd/S.

The most straightforward combination of $2\pi$ helical views from two linear detector arrays into a full-scan data set is employed in the first embodiment noted above. In this combination of views, those views taken at the same view angle and located on opposite sides of the slice midplane are linearly interpolated. The views are weighted inversely proportional to their distance from the midplane and the weighting is independent of ray angle. Since each view has a width 2d–dR/S and the first and last views are 2d apart, where (see FIG. 4 and FIG. 5) R= distance of Z-axis from the source 24, S= distance of detector from the source 24, and d= the source thickness, the effective slice incorporate data from within a thickness 4d–dR/S.

Figure 6:
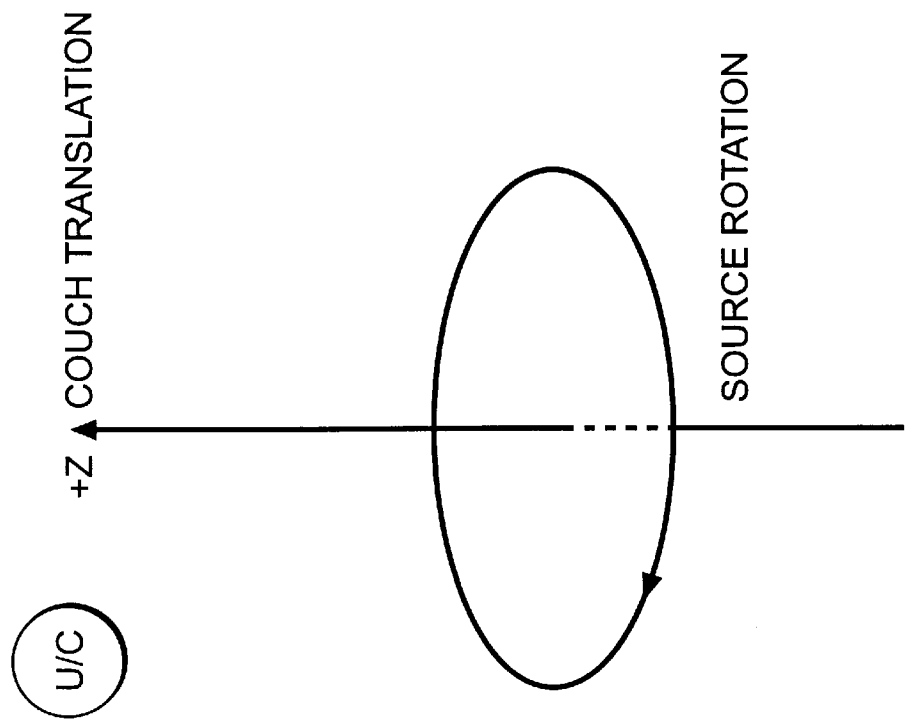
FIG. 6 is an illustration of the direction of couch advance and source rotation in an U/C (up/clockwise) scanning mode.

The data collection scheme assumed for the description of the first embodiment is one in which the source 24 and the detectors 26 and 28 rotate clockwise in the (x,y) plane and the couch 30 moves in the positive z direction, as shown in FIG. 6. Angles increase in the direction of the arrows shown in FIG. 7. This configuration is denoted U/C (up/clockwise). Changes required to treat three other possible combinations of source rotation and couch translation are considered subsequently herein.

The plane to be reconstructed is denoted by its distance from the starting position D 32 of the couch. The time period of each $2\pi$ rotation is denoted by $\tau$. The time T at which the X-ray source lies in the slice midplane is T=D$\tau$/(2d). The time $\tau$ is used as a reference parameter in the indexing of the views. Further, as a result of the helical path of the collected data, the start angle of each reconstructed image has a different phase, defined to be $\pi$D/d, which is accounted for in the data processing.

The rays in each view in the first embodiment are indexed by the time expired since the beginning of the scan and by their view angle. The rays in each view can also be indexed by their distance from the slice midplane and by their view angle.

Figure 8B:
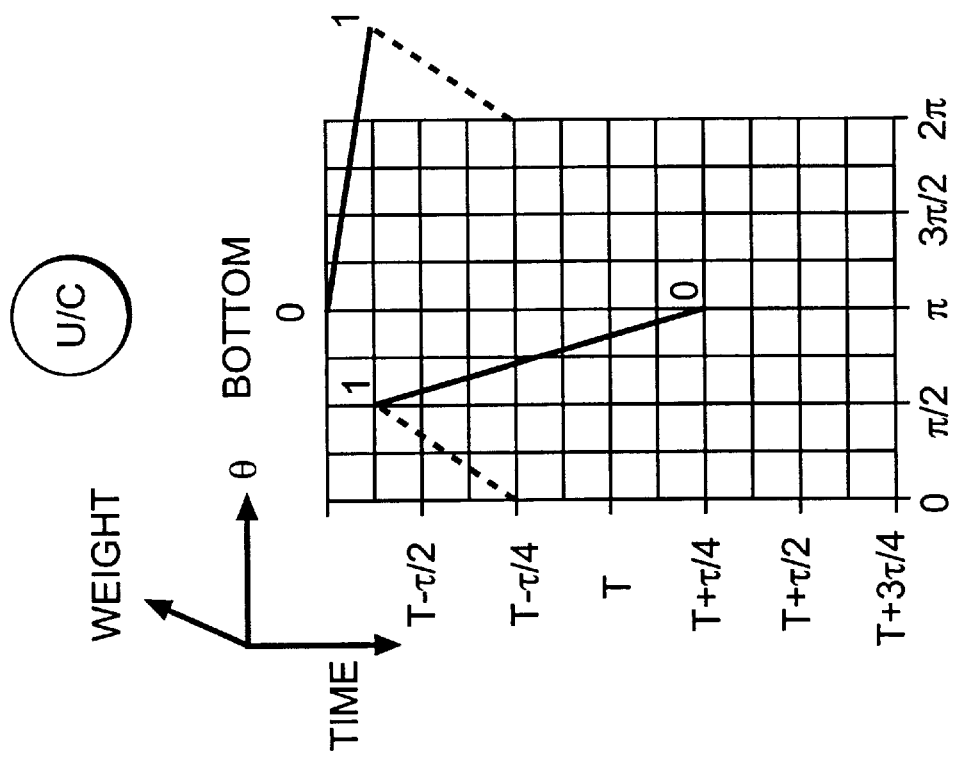
FIGS. 8a and 8b show diagrams of the interpolation weight as a function of elapsed time and view angle for a dual-detector-array, helical, full-scan reconstruction.
Figure 8A:
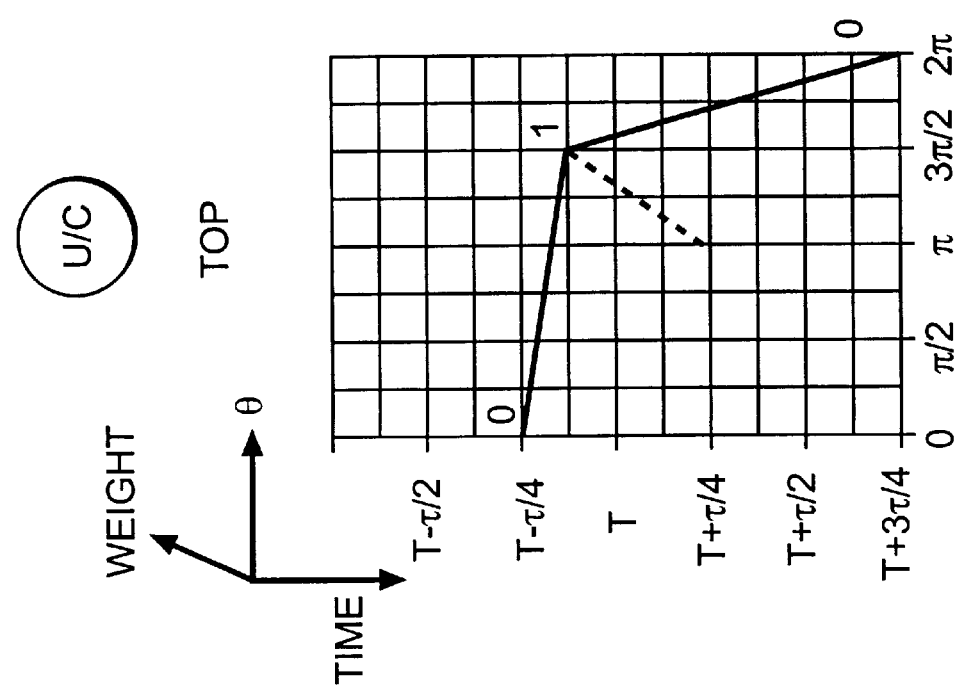
Figure 9B:
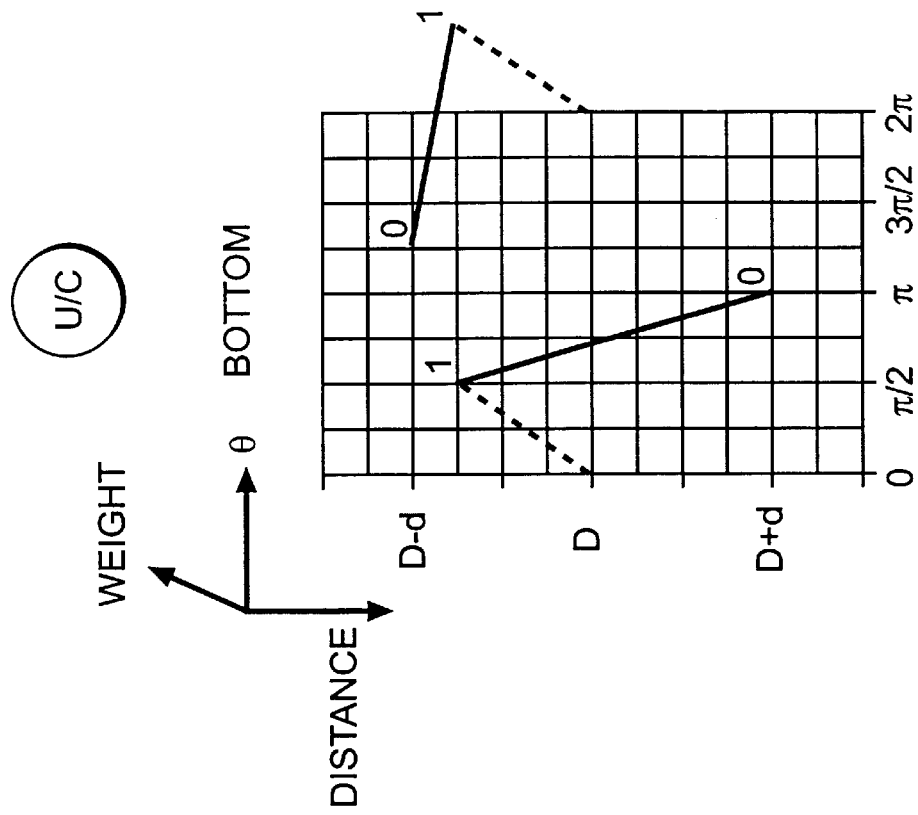
FIGS. 9a and 9b show diagrams of the interpolation wt. as a function of distance from scan start view angle for a dual-detector-array, helical, full-scan reconstruction.
Figure 9A:
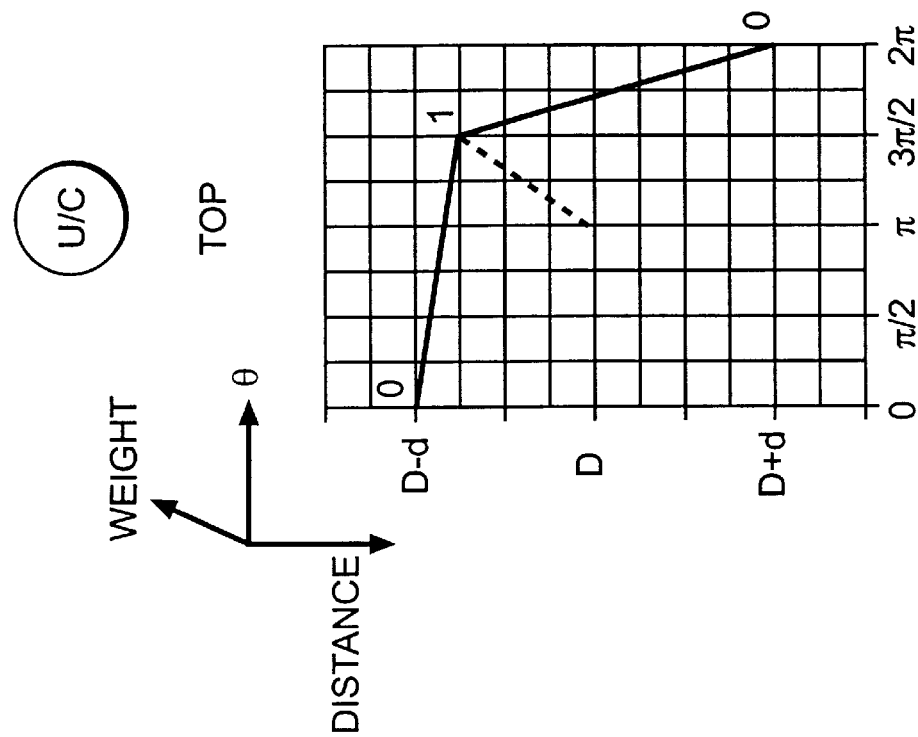

FIGS. 8 and 9 clarify the relationship between time and position. FIG. 8 shows the weight assigned to each view as a function of the view angle and the elapsed time for the two detector arrays, denoted TOP and BOTTOM. Data for $2\pi$ views is collected during a time interval 3r/2.

FIG. 9 shows the weight assigned to each view as a function of view angle and distance for the two detector arrays. Data for $2\pi$ views is collected over a translation distance 2d and during a time interval $3\tau/2$.

The formulas for combining the data to obtain $2\pi$ views for slice D are given by Equations (1) and (2) where $\Theta$ is the view angle and $\alpha$ is the ray angle.

$$P'\left(D, \Theta + \frac{\pi D}{d}, \alpha\right) = \left(\frac{\Theta}{\pi}\right)P^T\left(T - \frac{\tau}{4} + \frac{\Theta\tau}{2\pi}, \alpha\right) + \left(\frac{\pi - \Theta}{\pi}\right)P^B\left(T - \frac{\tau}{4} + \frac{\Theta\tau}{2\pi}, \alpha\right) \quad (0 \leq \Theta < \pi)U/C$$

Equation (1)

$$P'\left(D, \Theta + \frac{\pi D}{d}, \alpha\right) = \left(2 - \frac{\Theta}{\pi}\right)P^T\left(T - \frac{\tau}{4} + \frac{\Theta\tau}{2\pi}, \alpha\right) + \left(\frac{\Theta - \pi}{\pi}\right)P^B\left(T - \frac{5\tau}{4} + \frac{\Theta\tau}{2\pi}, \alpha\right) \quad (\pi \leq \Theta < 2\pi)U/C$$

Equation (2)

Implementing Equations (1) and (2) as they stand requires repeated searching through the detector data sets. It is preferable to multiply each ray in the data set by the sum total of its weights before convolution filtering, and back-project it from its usual position.

Figure 10:
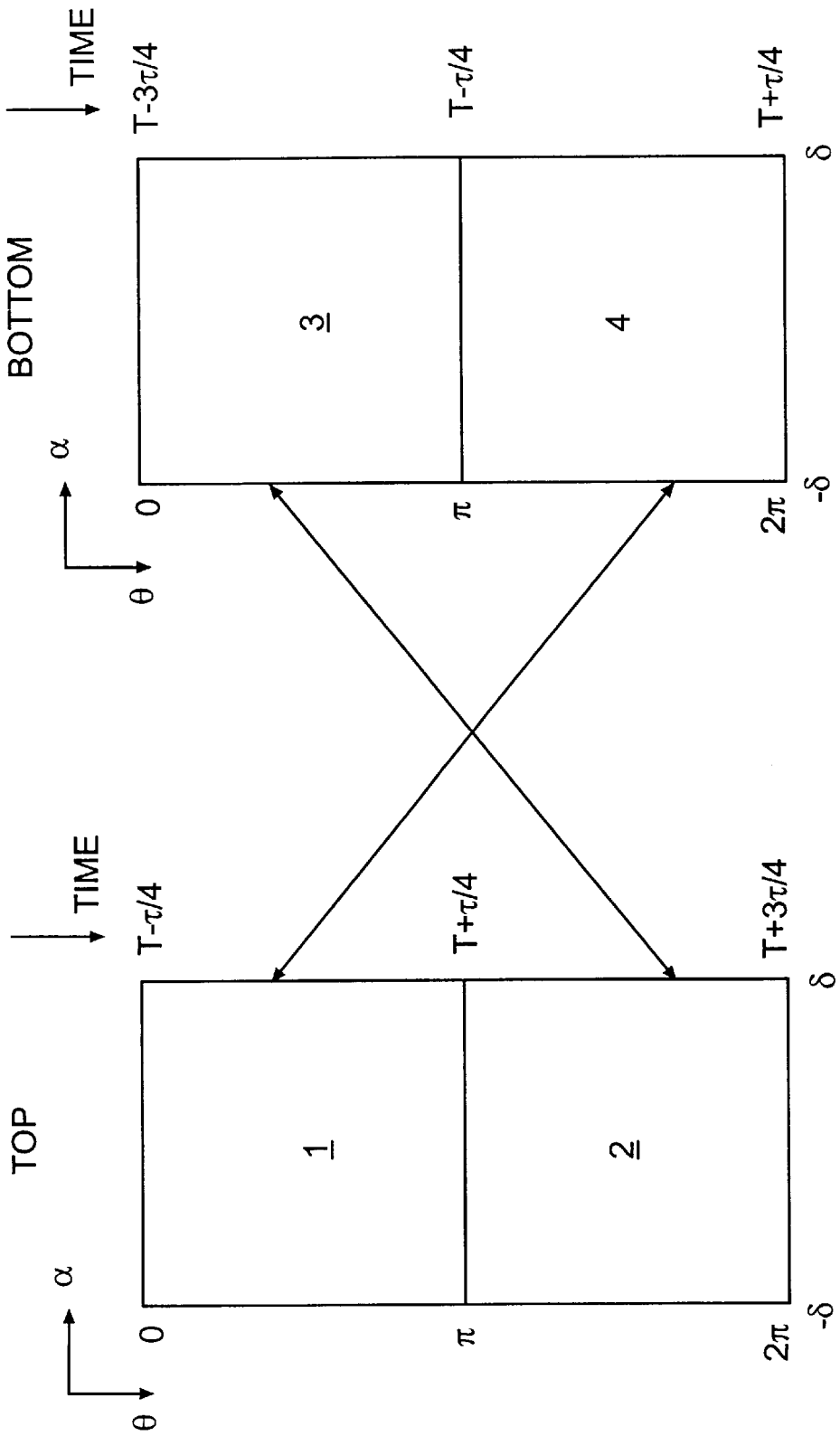
FIG. 10 shows a Radon-space diagram of data collection for the dual-detector-array, helical, full-scan reconstruction; region (1) of the TOP detector and region (4) of the BOTTOM detector share the same view orientation; and region (2) of the TOP detector and region (3) of the BOTTOM detector share the same view orientation.

FIG. 10 shows the Radon space description of data for dual-detector, helical scans. TOP detector data is collected when $0 \leq \Theta \leq \pi$ falls within region 1. BOTTOM detector data is collected when $0 \leq \Theta \leq \pi$ falls within region 3. TOP detector data is collected when $\pi \leq \Theta \leq 2\pi$ falls within region 2. BOTTOM detector data is collected when $\pi \leq \Theta \leq 2\pi$ falls within region 4.

Figure 7:
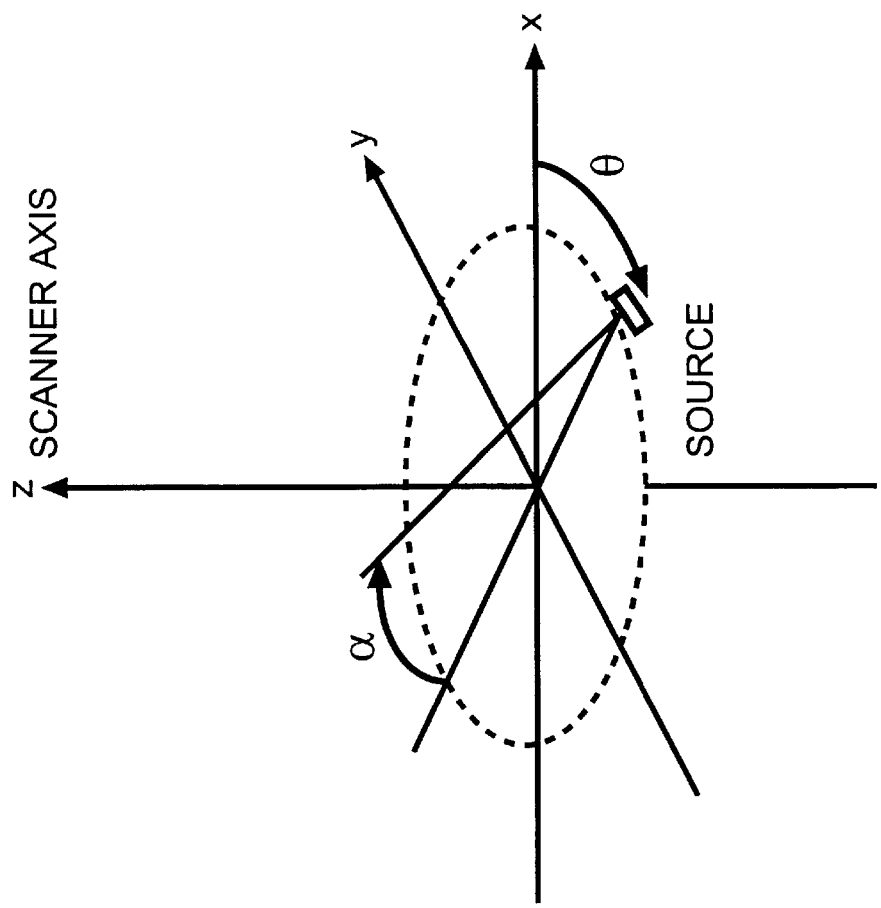
FIG. 7 shows the definition of source angle θ and ray angle α in the U/C scanning mode.

The preceding discussion assumes the scanning U/C configuration shown in FIGS. 6 and 7. Three other possible scanning configurations are possible as illustrated in FIGS. 11, 12, and 13.

Figure 11B:
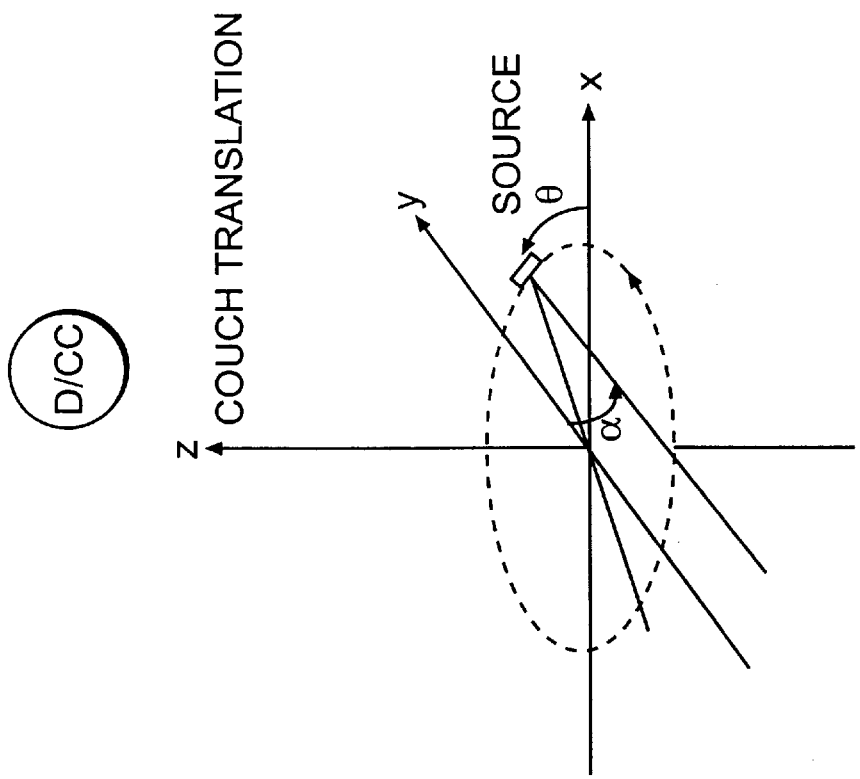
FIGS. 11a and 11b illustrate the direction of couch advancement, source rotation, and angle increase in a mode denoted D/CC (down/counter-clockwise)
Figure 11A:
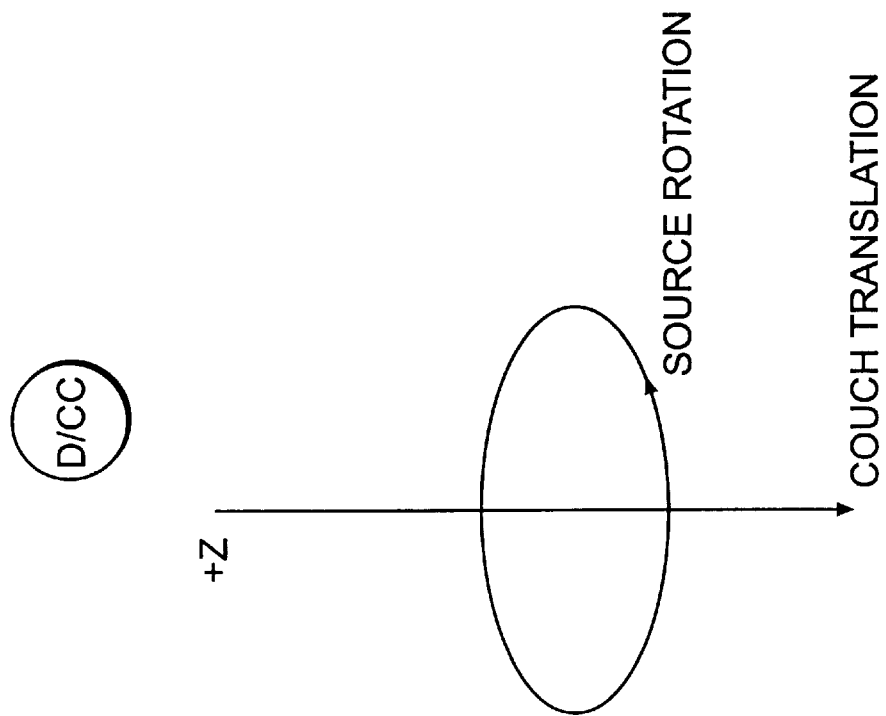

In the configuration depicted by FIG. 11, denoted D/CC, the source 24 rotates counter-clockwise and the couch 30 advances down the z axis. Equations (1) and (2) can be used to process this data if the TOP and BOTTOM detector array specifiers are exchanged.

Figure 12B:
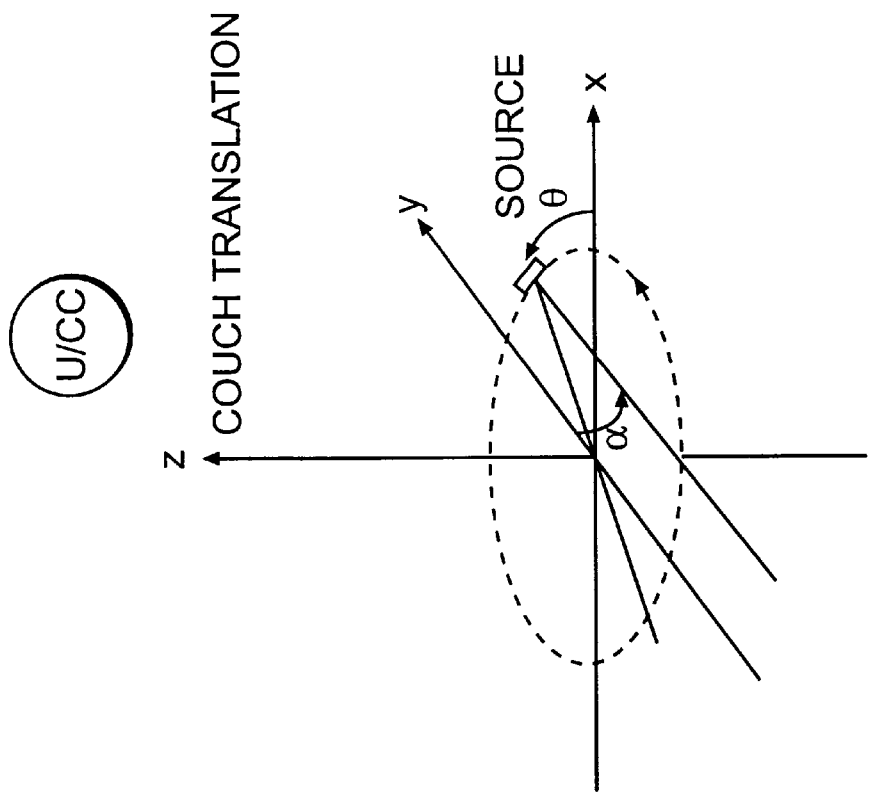
FIGS. 12a and 12b illustrate the direction of couch advancement, source rotation, and angle increase in a mode denoted U/CC (up/counter-clockwise)
Figure 12A:
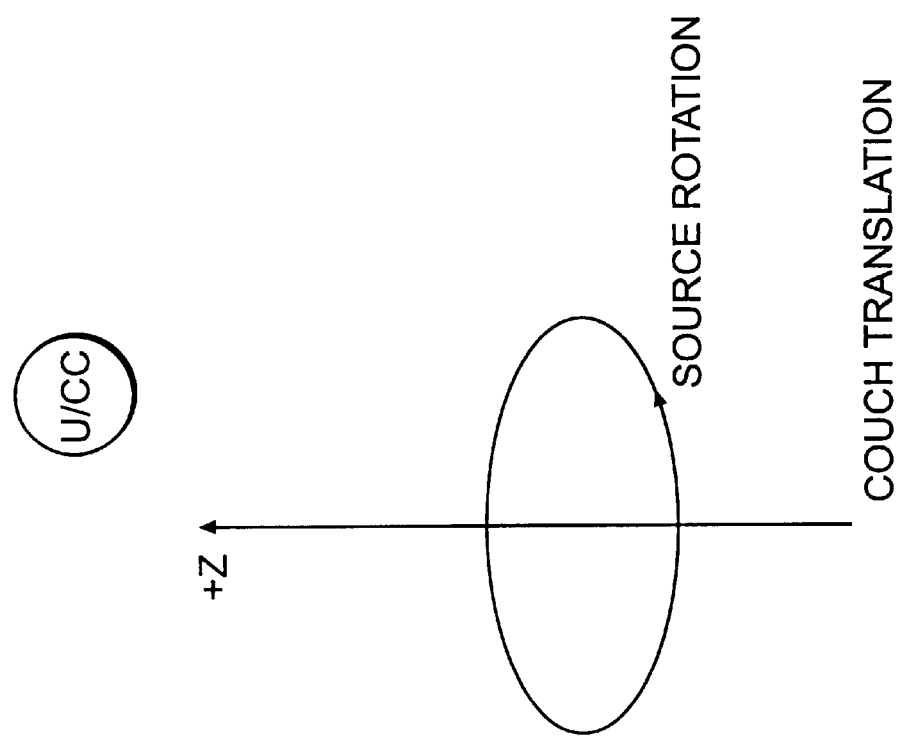

In the U/CC configuration depicted in FIG. 12, the source rotates counter-clockwise and the couch advances up the z axis. Equations (1) and (2) can also be used to process this data without change.

Figure 13B:
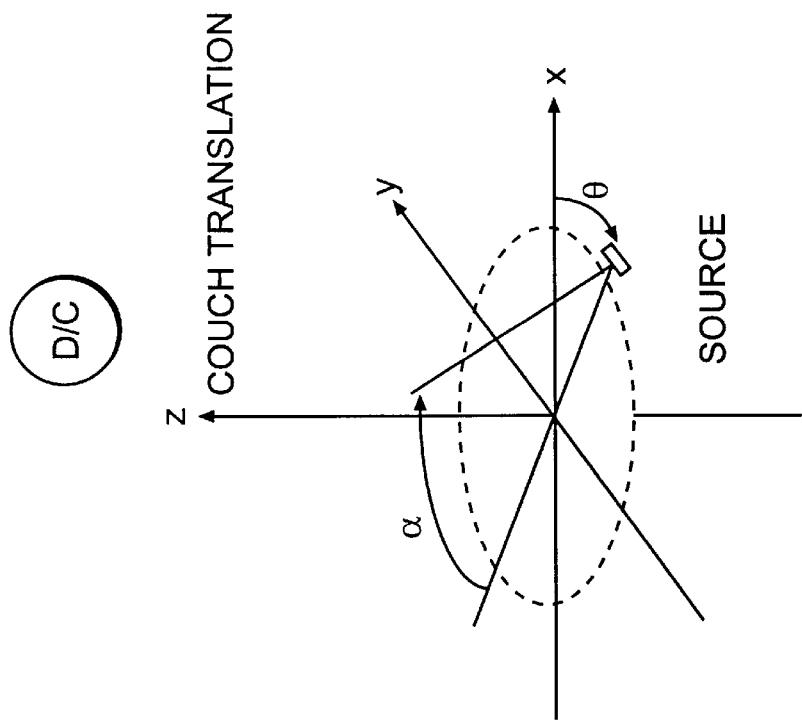
FIGS. 13a and 13b illustrate the direction of couch advancement, source rotation, and angle increase in a mode denoted D/C (down/clockwise)
Figure 13A:
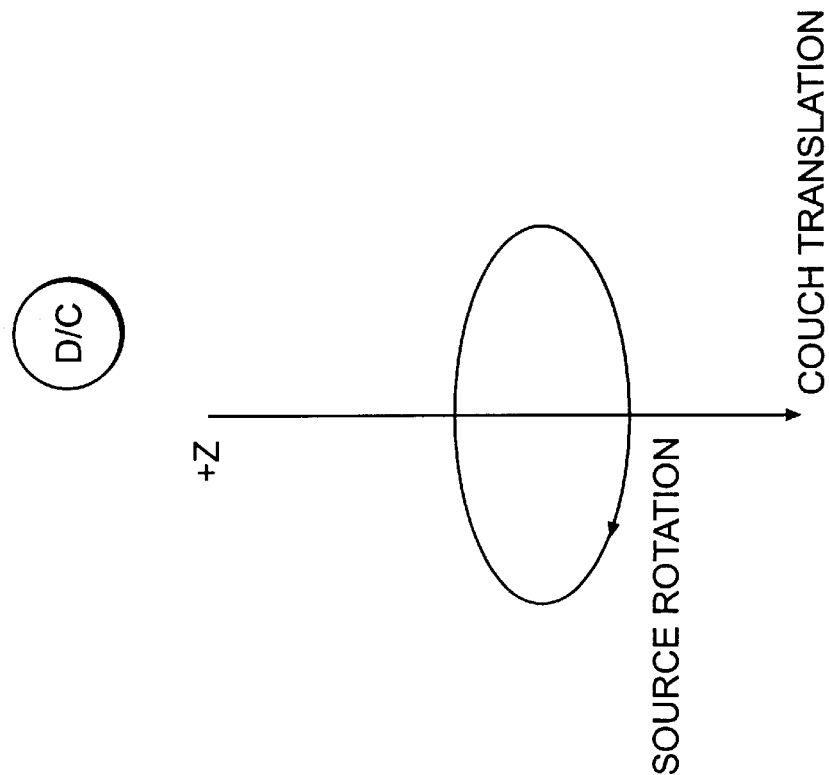

In the D/C configuration depicted by FIG. 13, the source rotates clockwise and the couch advances down the z axis. Equations (1) and (2) can be used to process this data if the TOP and BOTTOM detector specifiers are exchanged.

In the description that follows, the U/C configuration is assumed, but the formulas can be used for the other three configurations in an analogous manner.

Figure 14:
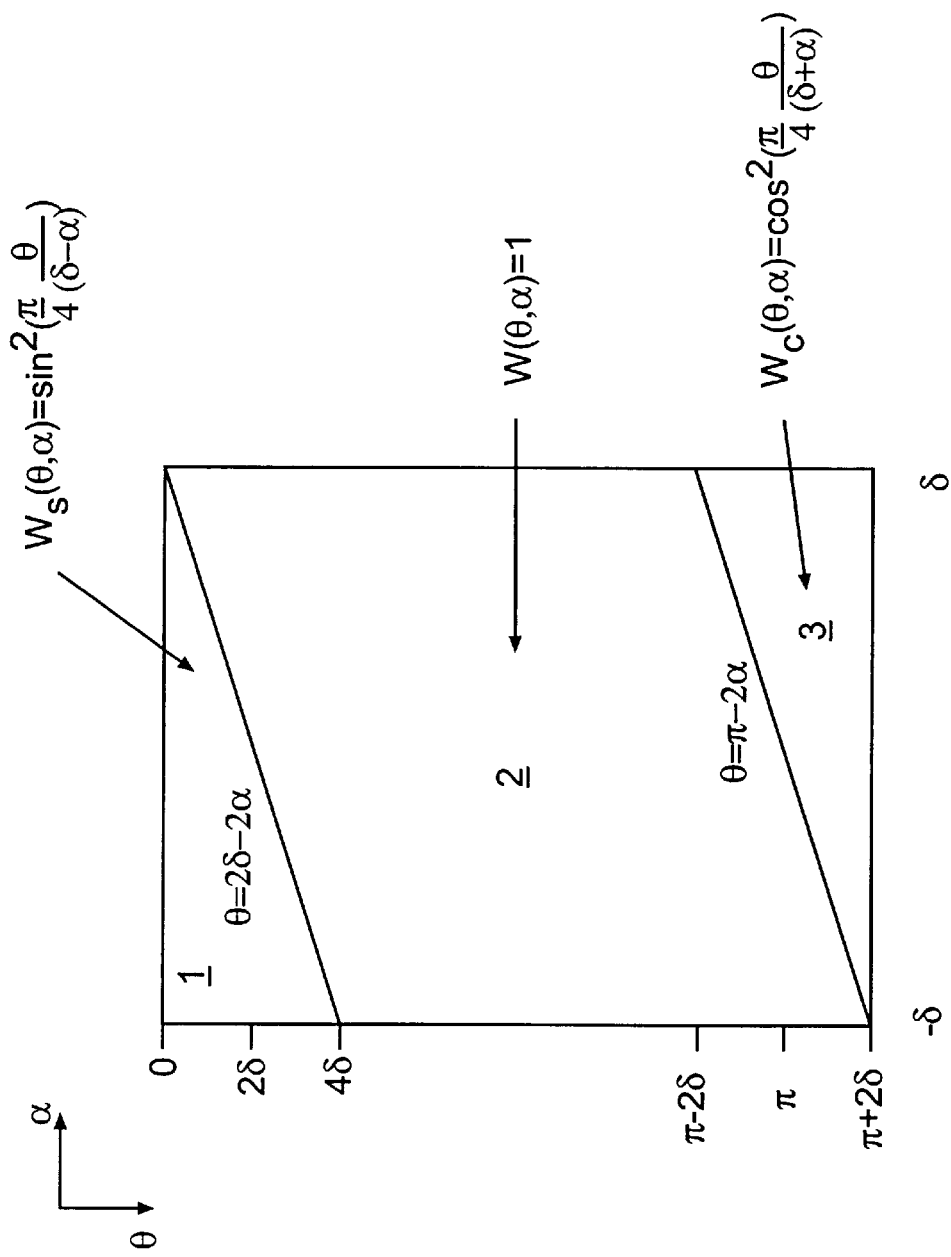
FIG. 14 shows a Radon-space diagram of half-scan reconstruction data for a dual-detector-array, helical scan, with data in regions (1) and (3) being redundant.

CT images reconstructed according to the first embodiment will be free of artifacts, but will not exhibit the minimum slice thickness that can be obtained. In a second embodiment, the data can be combined to form the minimal set of views taken over $\pi$ plus the detector fan angle $2\delta$. The effective slice width incorporates data from a region 3d+2$\delta$d/$\pi$–dR/S in width. The minimal data set is illustrated by the Radon space drawing in FIG. 14. $\Theta$ is the view angle, $\alpha$ is the ray angle, and $\delta$ is the maximum value of $\alpha$. In FIG. 14, the data in regions (1) and (3) are redundant. A good reconstruction can be obtained by weighting the data in these regions according to Table (1) and backprojecting views taken over $\pi$+2$\delta$. This weighting depends upon the angle of the ray as well as the angle of the view.

TABLE 1

| Region | View Angle | Weight |
|---|---|---|
| (1) | $0 \leq \Theta \leq 2\delta - 2\alpha$ | $\sin^2(\pi\Theta/(4(\delta - \alpha)))$ |
| (2) | $2\delta - 2\alpha \leq \Theta \leq \pi - 2\alpha$ | 1 |
| (3) | $\pi - 2\alpha \leq \Theta \leq \pi + 2\delta$ | $\cos^2(\pi(\Theta + 2\alpha - \pi)/(4(\delta + \alpha)))$ |

Weights other than the weights in TABLE 1 can be used for half scans. Simply setting one set of redundant data to zero causes streaks in a reconstruction, but other sets of weights and even simple feathering of the data in region 3 to zero can be used.

Figure 15B:
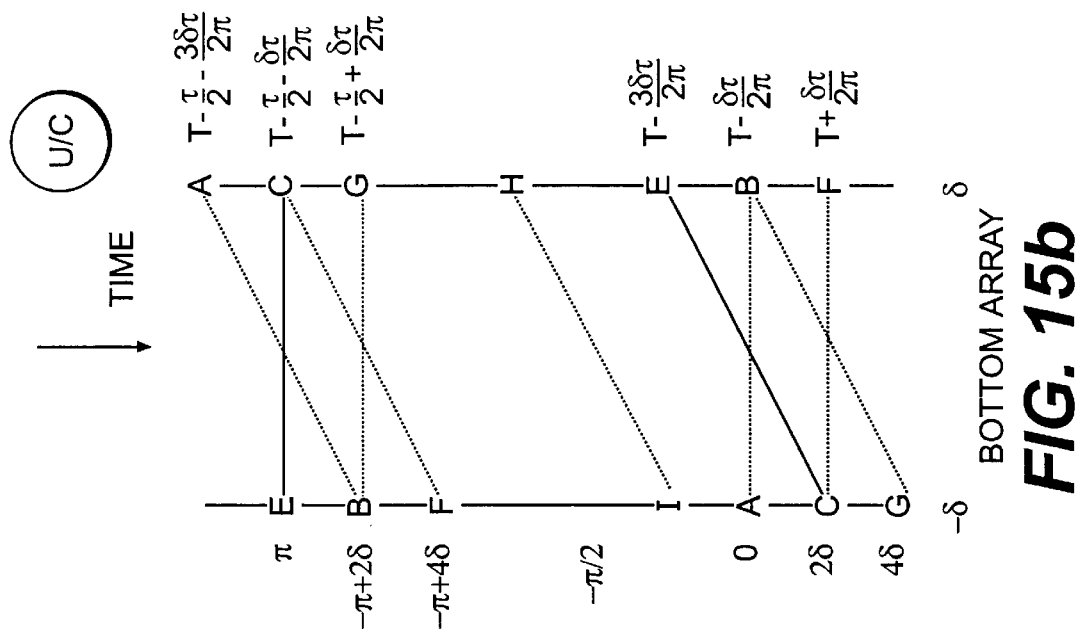
FIGS. 15a and 15b show a Radon-space diagram of the data from each detector array that is combined to form the dual-detector-array, half-scan reconstruction of a slice centered a distance D from the starting position, with lines drawn between the same two letters representing redundant data.
Figure 15A:
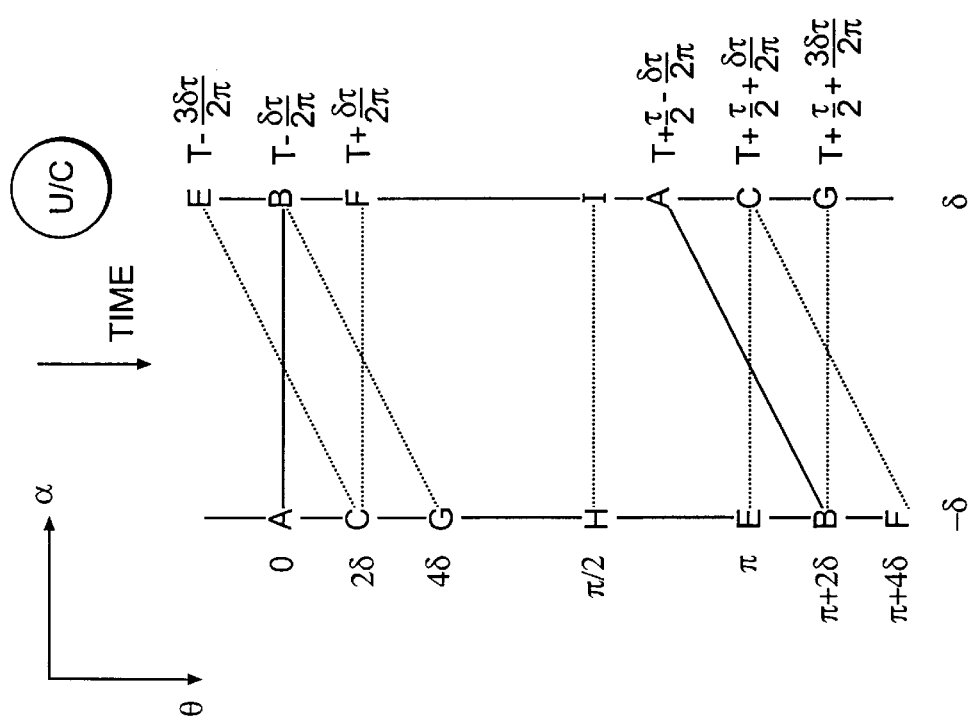

The second embodiment entails interpolation of views from both the TOP and BOTTOM detectors and from the top and bottom of the slice into the starting and ending views. FIG. 15 illustrates the method of data combination. The center of the slice occurs at a distance D=2dT/τ from the starting position, where T is the time at which the x-ray source lies in the slice midplane. Here, Θ is the view angle and α is the ray angle. The maximum ray half angle is ±δ.

The views are centered in regions that extend a distance ±(d/2+δd/π) on either side of D. Because each beam is about 2–dR/S in width, the data spans a region about 3d+2δd/π–dR/S in width. Streak artifacts are avoided by forming each view from a combination of one or two views from each detector array.

At the beginning and end of the data set, one regular view and one reflected view from each detector array are incorporated into each composite view so that the data joins smoothly. Intermediate views are formed from the average of one regular view from the TOP detector array and one reflected view from the BOTTOM detector array. In addition to smoothing time and position discontinuities, this method has the advantage of averaging differences in calibration between the two detector arrays, since each ray has contributions from both.

An illustration is given in FIG. 15 for the first composite view, denoted by the line AB for which Θ=0° (plus the phase angle πD/d). Data from this angle is taken at time T-δτ/(2π) by the TOP detector array and at time T-δτ/(2π) by the BOTTOM detector array. In addition, there is a reflected view taken by the TOP detector array that spans the time interval from T+τ/2−(δτ/2π) to T+τ/2+(3δτ/2π) and a reflected view taken by the BOTTOM detector that spans the time interval from T−τ/2−3δτ/(2π) to T−τ/2+δτ/2τ. These are weighted linearly with respect to their distance from the center of the slice and averaged as shown in Equation (3) for views from Θ=0 to Θ=2δ. To simplify the process, the reflected views are weighted by the distance of the center ray (α=0) from the slice midplane.

$$P'\left(D, \Theta + \frac{\pi D}{d}, \alpha\right) = \frac{1}{2}P^T\left(T - \frac{\delta\tau}{2\pi} + \frac{\Theta\tau}{2\pi}, \alpha\right)\left(\frac{\frac{\pi}{2} + \Theta - \delta}{\pi}\right) + \quad \text{Equation (3)}$$

$$\frac{1}{2}P^B\left(T - \frac{\delta\tau}{2\pi} + \frac{\Theta\tau}{2\pi}, \alpha\right)\left(\frac{\frac{\pi}{2} + \delta - \Theta}{\pi}\right) +$$

$$\frac{1}{2}P^T\left(T - \frac{\delta\tau}{2\pi} + \frac{(\Theta + \pi + 2\alpha)\tau}{2\pi}, -\alpha\right)\left(\frac{\frac{\pi}{2} + \delta - \Theta}{\pi}\right) +$$

$$\frac{1}{2}P^B\left(T - \frac{\delta\tau}{2\pi} + \frac{(\Theta - \pi + 2\alpha)\tau}{2\pi}, -\alpha\right)\left(\frac{\frac{\pi}{2} + \Theta - \delta}{\pi}\right)$$

$$0 \le \Theta \le 2\delta$$

For views from Θ>2δ to Θ<π, only one regular view is available from the TOP detector array and one reflected view is available from the BOTTOM detector array. These are on the same side of the slice center and are simply averaged as shown in Equation (4). The angle Θ=2δ is described by Equation (3) and the angle Θ=π is described by Equation (5).

$$P'\left(D, \Theta + \frac{\pi D}{d}, \alpha\right) = \frac{1}{2}P^T\left(T - \frac{\delta\tau}{2\pi} + \frac{\delta\Theta}{2\pi}, \alpha\right) + \quad \text{Equation (4)}$$

-continued $$\frac{1}{2}P^B\left(T - \frac{\delta\tau}{2\pi} + \frac{(\Theta - \pi + 2\alpha)\tau}{2\pi}, -\alpha\right) \quad 2\delta < \Theta < \pi$$

For views from Θ=π to Θ=π2δ, two views are again available from each detector array and these are linearly weighted with respect to their distance from the center of the slice and average as shown in Equation (5).

$$P'\left(D, \Theta + \frac{\pi D}{d}, \alpha\right) = \frac{1}{2}P^T\left(T - \frac{\delta\tau}{2\pi} + \frac{\Theta\tau}{2\pi}, \alpha\right)\left(\frac{\frac{3\pi}{2} - \Theta + \delta}{\pi}\right) + \quad \text{Equation (5)}$$

$$\frac{1}{2}P^B\left(T - \frac{\delta\tau}{2\pi} + \frac{(\Theta - 2\pi)\tau}{2\pi}, \alpha\right)\left(\frac{\Theta - \delta - \frac{\pi}{2}}{\pi}\right) +$$

$$\frac{1}{2}P^T\left(T - \frac{\delta\tau}{2\pi} + \frac{(\Theta - \pi + 2\alpha)\tau}{2\pi}, -\alpha\right)\left(\frac{\Theta - \delta - \frac{\pi}{2}}{\pi}\right) +$$

$$\frac{1}{2}P^B\left(T - \frac{\delta\tau}{2\pi} + \frac{(\Theta - \pi + 2\alpha)\tau}{2\pi}, -\alpha\right)\left(\frac{\frac{3\pi}{2} - \Theta + \delta}{\pi}\right)$$

$$\pi \le \Theta \le \pi + 2\delta$$

Figures 16A, 16B:
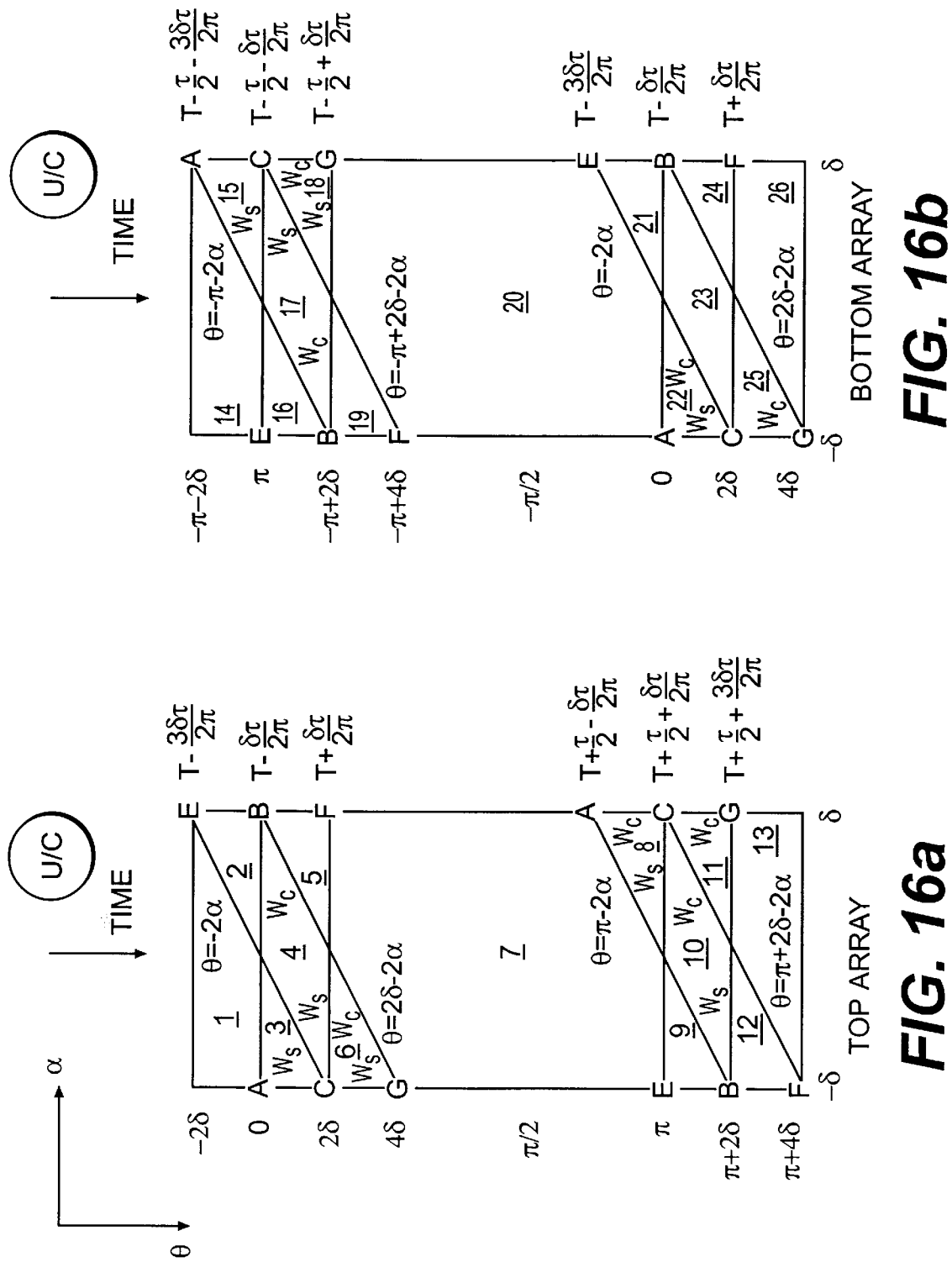
FIGS. 16a and 16b illustrates a division of the Radon-space diagram into 26 regions for the dual-detector-array, half-scan reconstruction, each requiring a different weighting function, with the symbols $w_s(w_c)$ denoting sine(cosine) weighting to remove data redundancy.

Implementing Equations (3)–(5) as they stand requires repeated searching through the detector data sets. It is preferable to merely multiply each ray in the set by the sum total of its weights before convolution and backproject it from its regular position. Because of the smoothing techniques used here, this weighting procedure is rather complicated. FIG. 16 illustrates the fact that the Radon space diagram for the two detector arrays can be divided into twenty-six regions in which the data have the same weights. In addition to the region number, some regions contain the annotation $w_c$ and/or $w_s$.

$w_c$ means that the region is to be additionally weighted by the cosine factor of Table 1 to eliminate data duplicity. $w_s$ means that the region is to be weighted by the sine factor of TABLE 1. Regions 1, 13, 14, and 26 have zero weighting.

Although the formulas for the data weights appear to be complicated, their implementation is straightforward. The weights are computed once and stored because only the phase of the view angle θ changes from slice to slice. It is also possible to eliminate the data regions numbered 2, and 12 by using duplicate regions within the (0,π+2δ) range for the TOP detector array and to eliminate the regions numbered 15, and 25 by using duplicate regions within the (−π, 2δ) range for the BOTTOM detector array. This reduces the slice width slightly, but negates some of the smoothing effects.

SUMMARY

The use of two, stacked, detector arrays enables helical-scan data to be collected in half the time required for single-detector-array, helical scanning.

This performance improvement is especially beneficial for medical tomography applications of the invention in which the invention enbales the scanning speed to be fast enough to provide data collection for a significant volume of the human chest during a single breath hold.

The foregoing description of the preferred embodiment has been presented to illustrate the invention. It is not intended to be exhaustive or to limit the invention to the form disclosed.

In applying the invention, modifications and variations can be made by those skilled in the pertaining art without departing from the scope and spirit of the invention. It is intended that the scope of the invention be defined by the claims appended hereto, and their equivalents.

What is claimed is:

1. A helical computerized tomography system in which an x-ray tube for radiating an x-ray and an object irradiated with the x-ray are relatively rotated with respect to each other, and the x-ray tube and the object are relatively moved along an axial direction of the object, thus performing a helical scan on the object, and the x-ray transmitted through the object is detected by an x-ray detector, thus reconstructing a tomograph at a desired position of a reference plane of reconstruction in the axial direction, said apparatus comprising:

a radiation detector arrangement having first and second array of detectors disposed along the axial direction of the object for collecting transmitted data of the x-ray transmitted through the object during the helical scan;

data extracting means for extracting first and second transmitted data each collected by said first and second arrays of detectors, the first and second transmitted data correspond to a same detector angle but different axial positions and the data extracting means extract one of the first and second transmitted data closer to the reference plane than the other;

means for interpolating projection data based on the first and second transmitted data extracted by said data extracting means to produce interpolated projection data at the position of the reference plane; and reconstructing means for reconstructing a tomogram at the position of the reference plane based on the interpolated projection data obtained by said interpolating means.

2. The helical tomography system of claim 1 wherein the following equations are employed by the interpolating means to combine the detector data:

$$P'\left(D, \Theta + \frac{\pi D}{d}, \alpha\right) = \left(\frac{\Theta}{\pi}\right) P^T\left(T - \frac{\tau}{4} + \frac{\Theta\tau}{2\pi}, \alpha\right) +$$
$$\left(\frac{\pi - \Theta}{\pi}\right) P^B\left(T - \frac{\tau}{4} + \frac{\Theta\tau}{2\pi}, \alpha\right) \quad (\Theta \leq \Theta < \pi) U/C$$

$$P'\left(D, \Theta + \frac{\pi D}{d}, \alpha\right) = \left(2 - \frac{\Theta}{\pi}\right) P^T\left(T - \frac{\tau}{4} + \frac{\Theta\tau}{2\pi}, \alpha\right) +$$
$$\left(\frac{\Theta - \pi}{\pi}\right) P^B\left(T - \frac{5\tau}{4} + \frac{\Theta\tau}{2\pi}, \alpha\right) \quad (\pi \leq \Theta < 2\pi) U/C$$

3. The helical tomography system of claim 1 wherein the angle formed by a ray extending between the x-ray tube and each detector and a reference ray from the x-ray tube to the detector arrangement is designated as $\alpha$, and wherein the interpolating means further comprises:

means for interpolating data values for each of a pair of detectors in the first and second arrays having the same angle $\alpha$, to the reference plane.

4. The helical tomography system of claim 3 wherein the interpolating means further comprises:

means for weighting each detector data value inversely proportional to the correlated distance for the data value from the reference plane.

5. The helical tomography system of claim 1 wherein the interpolating and weighting means interpolates data over a half scan path of 180 degrees plus an angle formed by the fan pattern.

6. The helical tomography system of claim 5 wherein the interpolating means employs the following equations:

$$P'\left(D, \Theta + \frac{\pi D}{d}, \alpha\right) = \frac{1}{2}P^T\left(T - \frac{\delta\tau}{2\pi} + \frac{\Theta\tau}{2\pi}, \alpha\right)\left(\frac{\frac{\pi}{2} + \Theta - \delta}{\pi}\right) +$$
$$\frac{1}{2}P^B\left(T - \frac{\delta\tau}{2\pi} + \frac{\Theta\tau}{2\pi}, \alpha\right)\left(\frac{\frac{\pi}{2} + \delta - \Theta}{\pi}\right) +$$
$$\frac{1}{2}P^T\left(T - \frac{\delta\tau}{2\pi} + \frac{(\Theta + \pi + 2\alpha)\tau}{2\pi}, -\alpha\right)\left(\frac{\frac{\pi}{2} + \delta - \Theta}{\pi}\right) +$$
$$\frac{1}{2}P^B\left(T - \frac{\delta\tau}{2\pi} + \frac{(\Theta - \pi + 2\alpha)\tau}{2\pi}, -\alpha\right)\left(\frac{\frac{\pi}{2} + \Theta - \delta}{\pi}\right) \quad 0 \leq \Theta \leq 2\delta$$

$$P'\left(D, \Theta + \frac{\pi D}{d}, \alpha\right) = \frac{1}{2}P^T\left(T - \frac{\delta\tau}{2\pi} + \frac{\delta\Theta}{2\pi}, \alpha\right) +$$
$$\frac{1}{2}P^B\left(T - \frac{\delta\tau}{2\pi} + \frac{(\Theta - \pi + 2\alpha)\tau}{2\pi}, -\alpha\right) \quad 2\delta < \Theta < \pi$$

$$P'\left(D, \Theta + \frac{\pi D}{d}, \alpha\right) = \frac{1}{2}P^T\left(T - \frac{\delta\tau}{2\pi} + \frac{\Theta\tau}{2\pi}, \alpha\right)\left(\frac{\frac{3\pi}{2} - \Theta + \delta}{\pi}\right) +$$
$$\frac{1}{2}P^B\left(T - \frac{\delta\tau}{2\pi} + \frac{(\Theta - 2\pi)\tau}{2\pi}, \alpha\right)\left(\frac{\Theta - \delta - \frac{\pi}{2}}{\pi}\right) +$$
$$\frac{1}{2}P^T\left(T - \frac{\delta\tau}{2\pi} + \frac{(\Theta - \pi + 2\alpha)\tau}{2\pi}, -\alpha\right)\left(\frac{\Theta - \delta - \frac{\pi}{2}}{\pi}\right) +$$
$$\frac{1}{2}P^B\left(T - \frac{\delta\tau}{2\pi} + \frac{(\Theta - \pi + 2\alpha)\tau}{2\pi}, -\alpha\right)\left(\frac{\frac{3\pi}{2} - \Theta + \delta}{\pi}\right) \quad \pi \leq \Theta \leq \pi + 2\delta$$

7. The helical tomography system of claim 1 wherein the interpolating means interpolates and weights data over a full scan path of 360 degrees.

8. The helical tomography system of claim 7 wherein each ray is multiplied by the sum of associated data weights before convolution.

9. The helical tomography system of claim 8 wherein the weight sums are defined by the following table:

| Region | View Angle | Weight |
|---|---|---|
| (1) | $0 \leq \Theta \leq 2\delta - 2\alpha$ | $\sin^2(\pi\Theta/(4(\delta - \alpha)))$ |
| (2) | $2\delta - 2\alpha \leq \Theta \leq \pi - 2\alpha$ | 1 |
| (3) | $\pi - 2\alpha \leq \Theta \leq \pi + 2\delta$ | $\cos^2(\pi(\Theta + 2\alpha - \pi)/(4(\delta + \alpha)))$ |

10. A method for operating a helical computerized tomography system in which an x-ray tube for radiating an x-ray and an object irradiated with the x-ray are relatively rotated with respect to each other, and the x-ray tube and the object are relatively moved along an axial direction of the object, thus performing a helical scan on the object, and the x-ray transmitted through the object is detected by an x-ray detector, thus reconstructing a tomograph at a desired position of a reference plane of reconstruction in the axial direction, said method comprising the steps of:

operating a radiation detector arrangement having a first and second array of detectors disposed along the axial direction of the object to collect transmitted data of the x-ray transmitted through the object during the helical scan;

extracting a first and second transmitted data each collected by said first and second array of detectors, the first and second transmitted data corresponding to a same detector angle but different axial position, and one of the transmitted data being extracted closer to the reference plane than the other;

interpolating a projection data based on the extracted first and second transmitted data to produce an interpolated projection data at the position of the reference plane; and reconstructing a tomogram at the position of the reference plane based on the interpolated projection data.

* * * * *